United States Patent
Moyers

(10) Patent No.: US 7,331,713 B2
(45) Date of Patent: Feb. 19, 2008

(54) METHOD AND DEVICE FOR DELIVERING RADIOTHERAPY

(75) Inventor: Michael F. Moyers, Colton, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 11/314,138

(22) Filed: Dec. 21, 2005

(65) Prior Publication Data

US 2006/0215819 A1 Sep. 28, 2006

Related U.S. Application Data

(63) Continuation of application No. 10/887,507, filed on Jul. 7, 2004, now Pat. No. 7,011,447, which is a continuation of application No. 10/393,836, filed on Mar. 20, 2003, now Pat. No. 6,769,806, which is a continuation of application No. PCT/US02/34556, filed on Oct. 28, 2002.

(60) Provisional application No. 60/340,430, filed on Oct. 30, 2001.

(51) Int. Cl.
*A61B 6/08* (2006.01)
(52) U.S. Cl. .................. 378/205; 378/209; 378/65
(58) Field of Classification Search .............. 378/20, 378/64, 65, 68, 205, 208, 209; 5/601
See application file for complete search history.

(56) References Cited

U.S. PATENT DOCUMENTS

| | | | |
|---|---|---|---|
| 3,397,411 A | 8/1968 | Rossi | 5/601 |
| 5,048,071 A | 9/1991 | Van Steenburg | 378/209 |
| 5,156,166 A | 10/1992 | Sebring | 5/608 |
| 5,570,409 A | 10/1996 | Yamaguchi et al. | 378/196 |
| 5,911,655 A | 6/1999 | Brenneisen | 5/622 |
| 6,094,760 A | 8/2000 | Nonaka et al. | 5/601 |
| 6,195,578 B1 | 2/2001 | Distler et al. | 600/415 |
| 6,244,745 B1 | 6/2001 | Mattern | 378/209 |
| 6,275,564 B1 | 8/2001 | Ein-Gal | 378/68 |
| 6,375,355 B1 | 4/2002 | Fortin | 378/209 |
| 6,460,206 B1 * | 10/2002 | Blasche et al. | 5/601 |
| 6,769,806 B2 * | 8/2004 | Moyers | 378/204 |

FOREIGN PATENT DOCUMENTS

| | | |
|---|---|---|
| DE | 44 18 216 A1 | 11/1995 |
| EP | 0 283 082 A1 | 9/1988 |
| WO | WO 01/89625 A2 | 11/2001 |

* cited by examiner

*Primary Examiner*—Courtney Thomas
(74) *Attorney, Agent, or Firm*—Knobbe Martens Olson & Bear LLP

(57) ABSTRACT

A device 10 for aligning a patient for delivering a plurality of radiation beams comprising a patient support surface 12, a coarse alignment subsystem 14 connected to the patient support surface, and a fine alignment subsystem connected to the patient support surface 16. A method of aligning a patient for delivering a plurality of radiation beams from a plurality of device positions comprising compensating for flexion of a radiation beam delivery device within a gantry during movement of the radiation beam delivery device from a first device position to a second device position by using a set of predetermined data describing the flexion behavior of the radiation beam delivery device so that the target tissue within the patient is placed at the beamline center for the radiation beam delivery device at the second device position.

15 Claims, 18 Drawing Sheets

FIG.12

PROVIDING A DEVICE FOR ALIGNING A PATIENT FOR DELIVERING A PLURALITY OF RADIATION BEAMS, THE DEVICE COMPRISING A PATIENT SUPPORT SURFACE, A COARSE ALIGNMENT SUBSYSTEM CONNECTED TO THE PATIENT SUPPORT SURFACE, AND A FINE ALIGNMENT SUBSYSTEM CONNECTED TO THE PATIENT SUPPORT SURFACE

COMPENSATING FOR FLEXION OF THE DEVICE DURING MOVEMENT OF THE DEVICE FROM A FIRST DEVICE POSITION TO A SECOND DEVICE POSITION BY USING A SET OF PREDETERMINED DATA DESCRIBING THE FLEXION BEHAVIOR OF THE DEVICE SO THAT TARGET TISSUE WITHIN THE PATIENT IS PLACED IN THE BEAMLINE CENTER FOR THE DEVICE AT THE SECOND DEVICE POSITION

FIG.13

PROVIDING A DEVICE FOR ALIGNING A PATIENT FOR DELIVERING A PLURALITY OF RADIATION BEAMS, THE DEVICE COMPRISING PATIENT SUPPORT MEANS, COARSE ALIGNMENT MEANS CONNECTED TO THE PATIENT SUPPORT MEANS, AND FINE ALIGNMENT MEANS CONNECTED TO THE PATIENT SUPPORT MEANS

COMPENSATING FOR FLEXION OF THE DEVICE DURING MOVEMENT OF THE DEVICE FROM A FIRST DEVICE POSITION TO A SECOND DEVICE POSITION BY USING A SET OF PREDETERMINED DATA DESCRIBING THE FLEXION BEHAVIOR OF THE DEVICE SO THAT TARGET TISSUE WITHIN THE PATIENT IS PLACED AT THE BEAMLINE CENTER FOR THE DEVICE AT THE SECOND DEVICE POSITION

FIG.14

COMPENSATING FOR FLEXION OF A RADIATION BEAM DELIVERY DEVICE HAVING A BEAMLINE CENTER DURING MOVEMENT OF THE RADIATION BEAM DELIVERY DEVICE FROM A FIRST DEVICE POSITION TO A SECOND DEVICE POSITION BY USING A SET OF PREDETERMINED DATA DESCRIBING THE FLEXION BEHAVIOR OF THE RADIATION BEAM DELIVERY DEVICE SO THAT THE TARGET TISSUE WITHIN THE PATIENT IS PLACED AT THE BEAMLINE CENTER FOR THE RADIATION BEAM DELIVERY DEVICE AT THE SECOND DEVICE POSITION

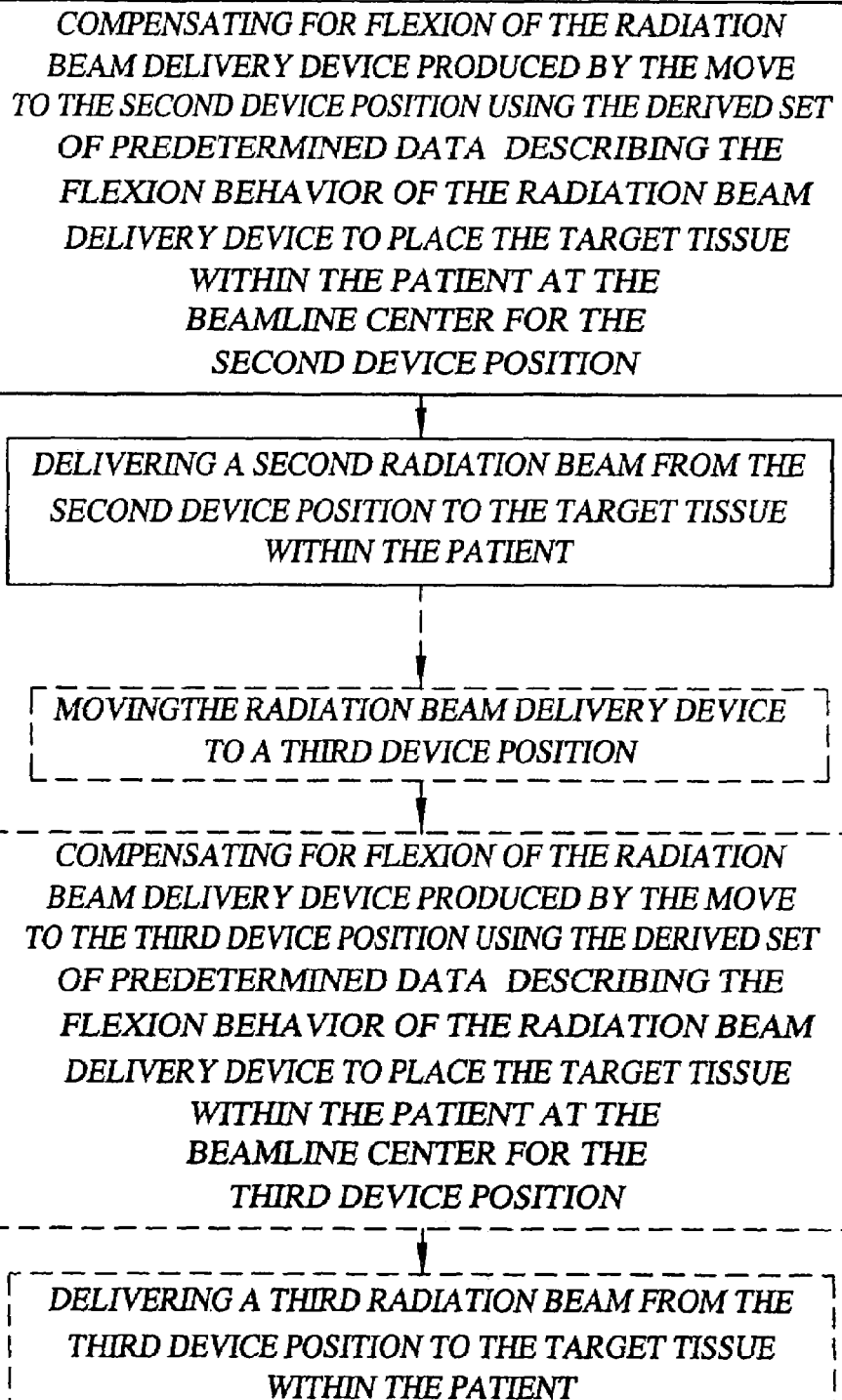

```
┌─────────────────────────────────────────────────────────┐
│ THE TARGET LOCATION WITHIN THE PATIENT IS DETERMINED    │
│      RELATIVE TO A REFERENCE POINT OF THE PATIENT       │
│                      POSITIONER.                        │
└─────────────────────────────────────────────────────────┘
                            │
┌─────────────────────────────────────────────────────────┐
│ THE ROOM COORDINATES FOR THE PATIENT POSITIONER COARSE ALIGNMENT │
│ SUBSYSTEM THAT ARE REQUIRED TO PLACE THE RADIATION BEAM DELIVERY │
│ DEVICE BEAMLINE CENTER AT THE TARGET LOCATION WITHIN THE PATIENT │
│    ARE CALCULATED, AND THESE COORDINATES ARE TRANSFERRED INTO A  │
│      PATIENT POSITIONER DATABASE TO GENERATE A POSITION FILE.    │
└─────────────────────────────────────────────────────────┘
                            │
┌─────────────────────────────────────────────────────────┐
│   THE PATIENT IS TAKEN TO THE TREATMENT ROOM AND THE PATIENT IS │
│ REGISTERED AND IMMOBILIZED TO THE PATIENT POSITIONER USING THE  │
│   IDENTICAL REGISTRATION AND IMMOBILIZATION DEVICES USED FOR    │
│              GENERATING THE TREATMENT PLAN.                     │
└─────────────────────────────────────────────────────────┘
                            │
┌─────────────────────────────────────────────────────────┐
│ THE FINE ALIGNMENT SUBSYSTEM IS CENTERED TO A NEUTRAL POSITION AND THE │
│  COARSE ALIGNMENT SUBSYSTEM IS USED TO PLACE THE TARGET TISSUE WITHIN  │
│    THE PATIENT CLOSE TO THE BEAMLINE CENTER FOR THE RADIATION BEAM     │
│    DELIVERY DEVICE USING THE REFERENCE POINT OF THE PATIENT POSITIONER.│
└─────────────────────────────────────────────────────────┘
                            │
┌─────────────────────────────────────────────────────────┐
│    TARGET TISSUE LOCATION IS DETERMINED USING CONVENTIONAL     │
│    METHODS, SUCH AS USING LOCALIZATION X-RAY IMAGES, AND ANY   │
│ DISCREPANCY BETWEEN THE TARGET TISSUE'S PRESENT LOCATION AND   │
│       THE TARGET TISSUE'S DESIRED LOCATION IS CALCULATED       │
└─────────────────────────────────────────────────────────┘
                            │
┌─────────────────────────────────────────────────────────┐
│    THE PATIENT POSITIONER FINE ALIGNMENT SUBSYSTEM IS   │
│  USED TO PLACE THE TARGET TISSUE WITHIN THE PATIENT AT  │
│  THE BEAMLINE CENTER FOR THE RADIATION BEAM DELIVERY    │
│           DEVICE AT THE FIRST DEVICE POSITION.          │
└─────────────────────────────────────────────────────────┘
```

FIGURE 18

METHOD AND DEVICE FOR DELIVERING RADIOTHERAPY

CROSS-REFERENCE TO RELATED APPLICATION

The present application is a continuation of U.S. Pat. application Ser. No. 10/887,507, filed Jul. 7, 2004 now U.S. Pat. No. 7,011,447 which was a continuation of U.S. application Ser. No. 10/393,836, filed Mar. 20, 2003, now U.S. Pat. No. 6,769,806, which is a continuation and which claims priority from International Pat. application PCT/US02/34556, titled "Method and Device for Delivering Radiotherapy," filed Oct. 28, 2002, which claims the benefit of U.S. Provisional Patent Application Ser. No. 60/340,430, filed Oct. 30, 2001, entitled "Method and Device for Delivering Radiotherapy," the contents of which are incorporated herein by reference in their entirety.

STATEMENT REGARDING FEDERALLY SPONSORED RESEARCH OR DEVELOPMENT

This invention was made with United States Government support under Cooperative Agreement Number DAMD17-97-2-7016 with the National Medical Technology Testbed, Inc., United States Department of the Army. The United States Government has certain rights in this invention.

BACKGROUND

The application of radiation is used for a variety of diagnostic and therapeutic purposes. For example, external radiotherapy known as "teletherapy" is used to treat approximately half of all patients with cancer in the United States, as well as being used to treat patients with arterio-venous malformations, intraocular subfoveal neovascular membranes and Parkinson's disease, among other diseases and conditions.

Generally, teletherapy has been performed using x-ray beams or electron beams. More recently, however, teletherapy has been performed using proton beams due to two characteristics of proton beams. First, proton beams do not scatter as much as either x-ray beams or electron beams. Thus, teletherapy with a proton beam can be applied with a steeper dose gradient near the edge of the proton beam than for an x-ray beam or electron beam. Second, protons lose energy at a more rapid rate as they penetrate tissue, thereby delivering a greater dose at the depth of the target tissue. These two characteristics of proton beams allow the delivery of higher doses to target tissues while minimizing radiation to adjacent normal tissues.

The delineation of target tissues from non-target tissues and the selection of beam directions is typically performed using a computerized treatment planning system. The computerized treatment planning system analyzes input information, such as x-ray axial computed tomography and magnetic resonance imaging, and provides output information, such as beam directions, shapes of normal tissue shields for each beam, and patient alignment information for each beam.

Regardless of the type of teletherapy, however, proper patient alignment is critical to delivering sufficient radiation to target tissues while minimizing radiation delivered to non-target tissues. Patient alignment is the process by which a. patient is reproducibly interfaced with the radiation delivery equipment for the purposes of obtaining anatomical, morphological, and physiological information, for performing treatment simulations, and for delivering treatments. The goals of patient alignment are to permit unrestricted access to the patient by radiation beams, and to provide accurate tissue targeting and dose delivery, while promoting patient comfort and safety, and allowing for quick patient egress from the radiation delivery equipment.

The five steps in the patient alignment process are registration, immobilization, localization, positioning and verification. Registration comprises placing the patient on a patient positioner, such as a movable table, in a reproducible manner. Immobilization comprises fixing the registered patient to the patient positioner so that they move together as a single unit in a controlled fashion. Localization comprises determining the location of the target tissue relative to the diagnostic, simulation or treatment unit. Positioning comprises moving the patient positioner to place the target tissue in the desired orientation at the desired location. Verification comprises verifying the patient's orientation and location, and can comprise using the same technique as localization. One or more than one of these steps can be repeated as required. If patient alignment is performed rapidly, the patient is more likely to remain properly aligned, minimizing the margin placed around the target tissue to account for motion and reducing the radiation dose to non-target tissues.

Patient alignment is usually performed with the patient in a supine position because a larger surface area of the patient is captured by registration and immobilization devices, because the entire patient is at a height more accessible to treatment personnel and because patients are generally more comfortable in the supine position. Most patient positioners have, therefore, been some form of a table.

Registration is typically accomplished using a registration device such as a low-density foam that is custom molded to the patient's shape and attached to the top of the patient positioner. The patient lies directly on the foam, preventing the patient from rolling and translating with respect to the patient positioner, and increasing patient comfort.

Immobilization is typically accomplished using a thermoplastic net that attaches to the patient positioner and that covers both the patient and the registration device. Alternatively, for teletherapy involving the head and neck, immobilization can be accomplished using a ring referred to as a 'halo' that is screwed into the patient's skull and then bolted to the patient positioner.

High precision localization and verification generally rely on radiographic techniques and fiducial markers. The fiducial markers can be internal, such as natural anatomical landmarks or implanted landmarks, or can be external such as a z-box attached to a halo.

Localization and verification for proton beam teletherapy typically uses proton beam treatment units that comprise a diagnostic x-ray source capable of projecting an x-ray beam to simulate the intended path of the proton beam. The x-ray beam passes through the patient creating localization images captured on film or by an electronic portal imaging device; Localization is achieved by comparing the localization images with digitally reconstructed radiographs (DRRS) generated by the treatment planning system. The patient is repositioned iteratively and new localization images are generated until coincidence of the localization images and digitally reconstructed radiographs are obtained thereby verifying the location.

After patient alignment has been completed, teletherapy is commonly performed using isocentric gantries that facilitate the entry of radiation beams into patients from multiple directions in a timely manner. A gantry is a mechanical device that houses a radiation beam delivery system, and comprises one or more than one instrument, such as a particle accelerator, an x-ray tube, a beam spreading device, beam limiting collimators, a particle range modifier, a fluence modifying device and a dose monitoring detector.

The rotation axes of the gantry and the patient positioner intersect at a point in space called the isocenter. The center of the target tissue within the patient is generally placed at the isocenter. Unfortunately, radiation beam delivery devices within the gantry are prone to flex when rotated and, thereby, cause misalignment of the radiation beam with the target tissue.

Historically, when radiation field alignment was not critical to avoid normal tissues adjacent to the target tissues, the edges of radiation fields were placed at large distances around the target tissue volumes to ensure that the target tissue would be hit regardless of the misalignment of the radiation beam due to deflections of the radiation beam delivery system. When critical normal tissues were adjacent to target tissues, however, precise alignment was achieved either by radiographically repositioning the patient for each individual beam or by using large, rigid, and complex mechanical structures to reduce deflections of radiation beam delivery system. Disadvantageously, however, radiographically repositioning a patient requires at least about 15 minutes to align each radiation beam prior to radiation delivery. Therefore, delivering six beams to a patient requires a total treatment time of at least about 1.5 hours. Hence, radiographically repositioning a patient for each radiation beam significantly limits the number of patients that can be treated by each treatment apparatus and increases the cost per treatment.

Therefore, it would be useful to have a method of aligning a patient for delivering multiple radiation beams, such as proton beams, that allows a patient to be aligned in less time between beam deliveries. Further, It would be useful to have a device for aligning a patient for delivering multiple radiation beams, such as proton beams, that allows a patient to be aligned in less time.

SUMMARY

According to one embodiment of the present invention, there is provided a device for aligning a patient for delivering a plurality of radiation beams. The device comprises a patient support surface, a coarse alignment subsystem connected to the patient support surface, and a fine alignment subsystem connected to the patient support surface. In one embodiment, the patient support surface comprises a table. In another embodiment, the coarse alignment subsystem can induce coarse movements of the patient support surface comprising translation motions of as large as about 2 m, and rotations of as large as about 60°. In another embodiment, the coarse alignment subsystem comprises an elevating column. In another embodiment, the coarse alignment subsystem further comprises a base and a plurality of wheels connected to the base. In another embodiment, the coarse alignment subsystem further comprises a base and a counterweight connected to the base. In another embodiment, the device further comprises electronics to control movement of the coarse alignment subsystem. In another embodiment, the coarse alignment subsystem comprises a position detection system to calculate the position of the device. In another embodiment, the device further comprises an interface for affixing one or more than one registration and immobilization device connected to the patient support surface. In a preferred embodiment, the fine alignment subsystem can induce fine movements of the patient support surface comprising translation motions as large as about ±20 mm with a resolution of between about 0.04 mm and 0.1 mm resolution in three perpendicular axes, and pitch and roll rotations as large as about ±5° with a resolution of between about 0.1° and 0.2°. In another preferred embodiment, the fine alignment subsystem can induce fine movements of the patient support surface comprising translation motions as large as about ±20 mm with about 0.05 mm resolution in three perpendicular axes, and pitch and roll rotations of as large as about ±5° with a resolution of about 0.1°. In another embodiment, the device further comprises electronics to control movement of the fine alignment subsystem.

According to another embodiment of the present invention, there is provided a device for aligning a patient for delivering a plurality of radiation beams comprising patient support means, coarse alignment means connected to the patient support means, and fine alignment means connected to the patient support means. In one embodiment, the patient support means comprises a table. In another embodiment, the coarse alignment subsystem can induce coarse movements of the patient support surface comprising translation motions of as large as about 2 m, and rotations of as large as about 60°. In another embodiment, the coarse alignment means comprises an elevating column. In another embodiment, the coarse alignment means further comprises a base and a plurality of wheels connected to the base. In another embodiment, the coarse alignment means further comprises a base and a counterweight connected to the base. In another embodiment, the device further comprises electronics to control movement of the coarse alignment means. In another embodiment, the coarse alignment means comprises a position detection system to calculate the position of the device. In another embodiment, the device further comprises an interface for affixing one or more than one registration and immobilization means connected to the patient support means. In a preferred embodiment, the fine alignment subsystem can induce fine movements of the patient support surface comprising translation motions as large as about ±20 mm with a resolution of between about 0.04 mm and 0.1 mm resolution in three perpendicular axes, and pitch and roll rotations as large as about ±5° with a resolution of between about 0.1° and 0.2°.

According to another embodiment of the present invention, there is provided a method of aligning a patient for delivering a plurality of radiation beams from a plurality of device positions comprising providing a device of the present invention. In one embodiment, the device has a beamline center, and the method additionally comprises compensating for flexion of the device during movement of the device from a first device position to a second device position by using a set of predetermined data describing the flexion behavior of the device so that target tissue within the patient is placed at the beamline center for the device at the second device position.

According to another embodiment of the present invention, there is provided a method of aligning a patient for delivering a plurality of radiation beams from a plurality of device positions comprising compensating for flexion of a radiation beam delivery device having a beamline center during movement of the radiation beam delivery device from a first device position to a second device position by using a set of predetermined data describing the flexion behavior of the radiation beam delivery device so that the target tissue within the patient is placed at the beamline center for the radiation beam delivery device at the second device position.

According to another embodiment of the present invention, there is provided a method of aligning a patient with a target tissue within the patient for delivering a plurality of radiation beams from a plurality of device positions. The method comprises, a) providing a radiation beam delivery device having a beamline center; b) deriving a set of predetermined data describing the flexion behavior of a radiation beam delivery device; c) selecting a patient having one or more than one target tissue suitable for receiving a plurality of radiation beams; d) producing a treatment plan; e) aligning the patient with respect to the radiation beam delivery device oriented at a first device position using the derived set of predetermined data describing the flexion behavior of the radiation beam delivery device to place the target tissue within the patient at the beamline center for the first device position; f) delivering a first radiation beam from the first device position to the target tissue; g) moving the radiation beam delivery device to a second device position; h) compensating for flexion of the radiation beam delivery device produced by the move to the second device position using the derived set of predetermined data describing the flexion behavior of the radiation beam delivery device to place the target tissue within the patient at the beamline center for the second device position; and i) delivering a second radiation beam from the second device position to the target tissue within the patient. In one embodiment, the method further comprises a) moving the radiation beam delivery device to a third device position; b) compensating for flexion of the radiation beam delivery device produced by the move to the third device position using the derived set of predetermined data describing the flexion behavior of a radiation beam delivery device to place the target tissue within the patient at the beamline center for the third device position; and c) delivering a third radiation beam from the third device position to the target tissue within the patient. In another embodiment, selecting a patient having one or more than one target tissue suitable for receiving a plurality of radiation beams comprises selecting a patient having one or more than one target tissue having a disease or condition amenable to teletherapy. The disease or condition can be selected from the group consisting of acoustic neuroma, adenocarcinoma, astrocytoma, chordoma, meningioma, nasopharyngeal carcinoma and pituitary adenoma. In another embodiment, aligning the patient with respect to the radiation beam delivery device oriented at a first device position comprises using a two-stage patient positioner. In another embodiment, compensating for flexion of the radiation beam delivery device produced by the move to the second device position comprises using a two-stage patient positioner and moving the patient and patient positioner as a unit. In another embodiment, compensating for flexion of the radiation beam delivery device produced by the move to the second device position comprises one or more than one action selected from the group consisting of shifting an aperture or block holding cone with respect to the beam delivery apparatus center, shifting the position of beam delivery apparatus defining collimators, and offsetting the scan pattern of a magnetically scanned beam.

FIGURES

These and other features, aspects and advantages of the present invention will become better understood with regard to the following description, appended claims, and accompanying figures where:

Figure 16:
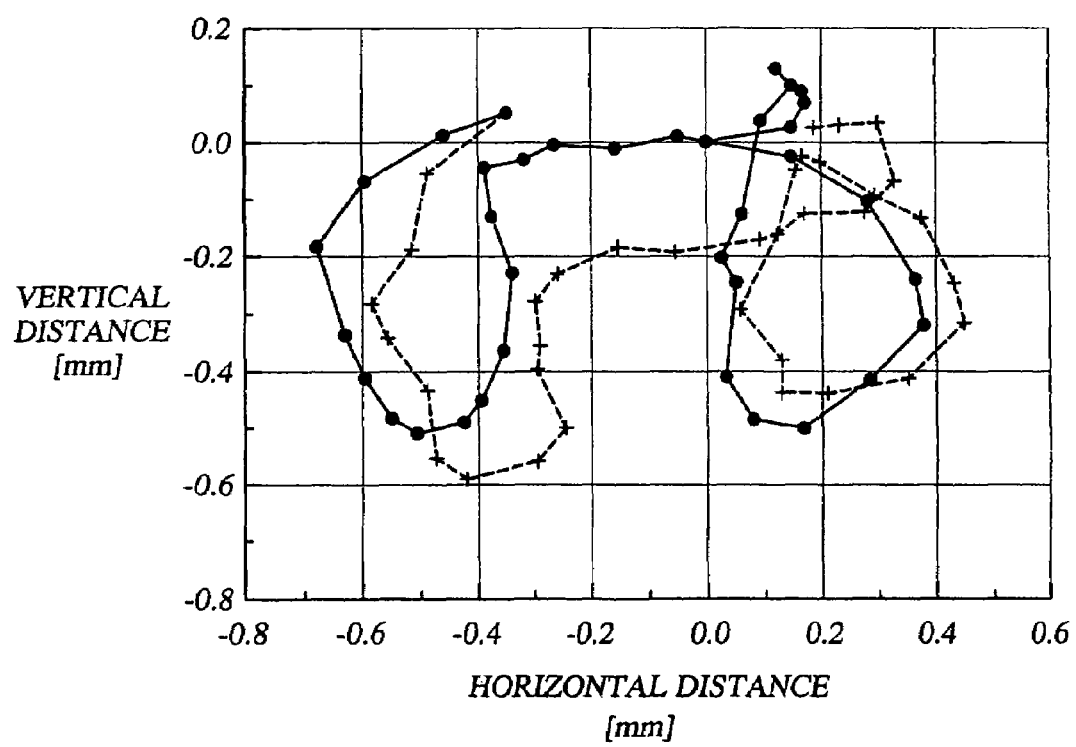
Figure 17:
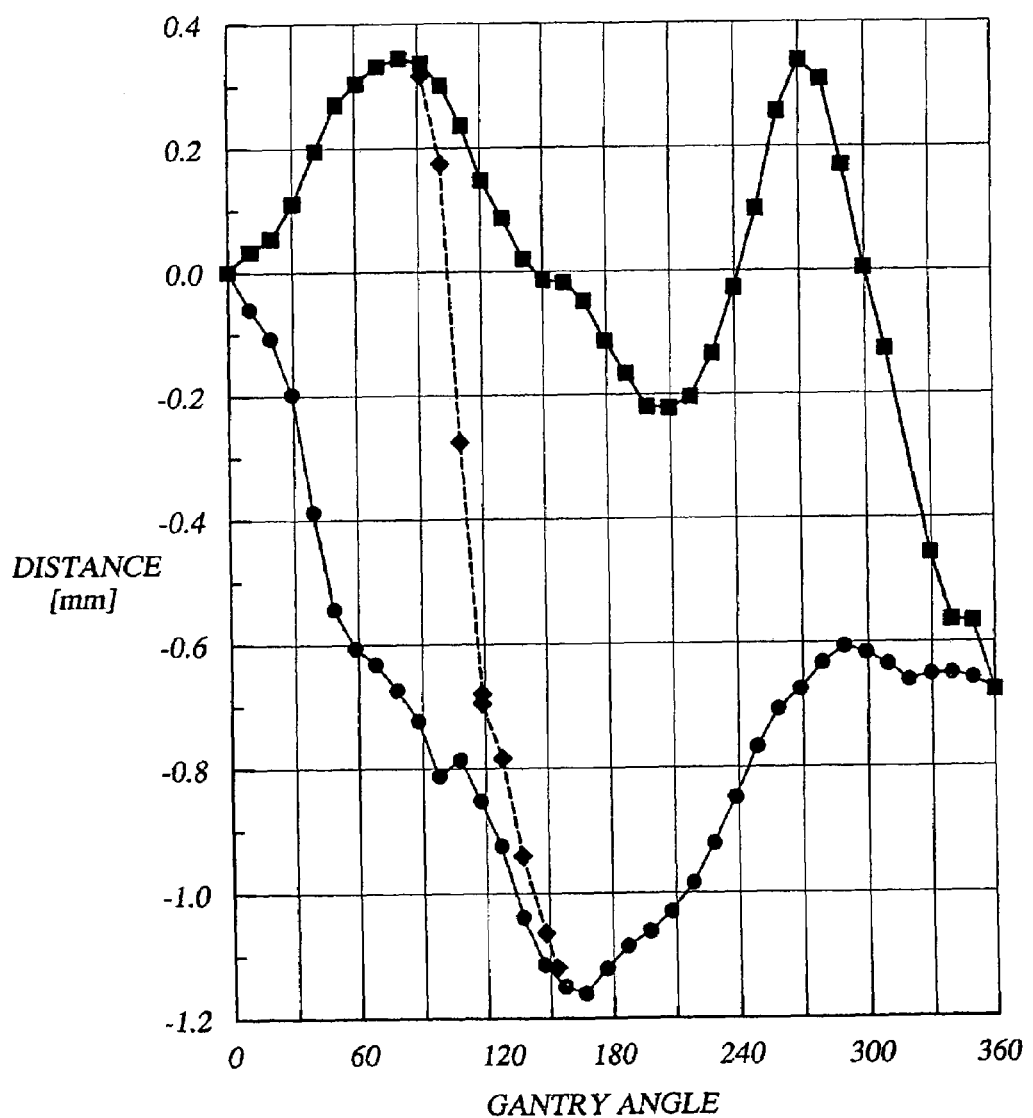

FIG. 12, FIG. 13, FIG. 14 and FIG. 15 are flow charts depicting some steps of various embodiments of the method of the present invention; and FIG. 16 and FIG. 17 are examples of plots of data sets describing the flexion behavior of a sample radiation beam delivery device in the plane of gantry rotation, and perpendicular to the plane of gantry rotation, respectively, that can be used with the method of alignment of the present invention.

FIG. 18 is a flowchart illustrating one embodiment of a method of positioning a patient for receiving radiation treatment.

DESCRIPTION

According to one embodiment of the present invention, there is provided a device for aligning a patient for delivering a plurality of radiation beams, such as proton beams, from a radiation beam delivery device at a plurality of device positions that allows a patient to be aligned in less time than using conventional aligning devices. According to another embodiment of the present invention, there is provided a method of aligning a patient for delivering a plurality of radiation beams, such as proton beams, from a radiation beam delivery device at a plurality of device positions. The method allows a patient to be aligned in less time than using conventional methods. By reducing the amount of time for alignment, both the device and the method allow an increased number of patients to be treated, decrease the cost of treatment per patient, and reduce the amount of radiation exposure to non-target tissues resulting from the alignment process. According to another embodiment of the present invention, there is provided a method of performing teletherapy. The method of performing teletherapy comprises aligning a patient using the method of aligning of the present invention and delivering a plurality of radiation beams from two or more than two directions. Though disclosed in connection with teletherapy, and especially teletherapy utilizing proton beams, the device and method can also be used for aligning a patient for delivering other kinds of radiation accurately and rapidly to a circumscribed area, for purposes other than teletherapy, as will be understood by those with skill in the art with reference to this disclosure.

In one embodiment, the present invention is a device for aligning a patient for delivering a plurality of radiation beams that takes less time to align the patient between each beam delivery than using conventional devices. The device can be used with the method of the present invention.

The device comprises a two-stage patient positioner. One stage comprises a coarse alignment subsystem capable of providing large traversals (defined as greater than about 2 m) and large rotations (defined as greater than about 5°) within the treatment room to place target tissue within the patient near the isocenter. The second stage comprises a fine alignment subsystem capable of submillimeter translations and subdegree size rotations to correct for any initial misalignments near isocenter, and to compensate for any deflections in the beam delivery device when a plurality of radiation beams is applied to the target tissue from a plurality of delivery directions.

Figure 1:
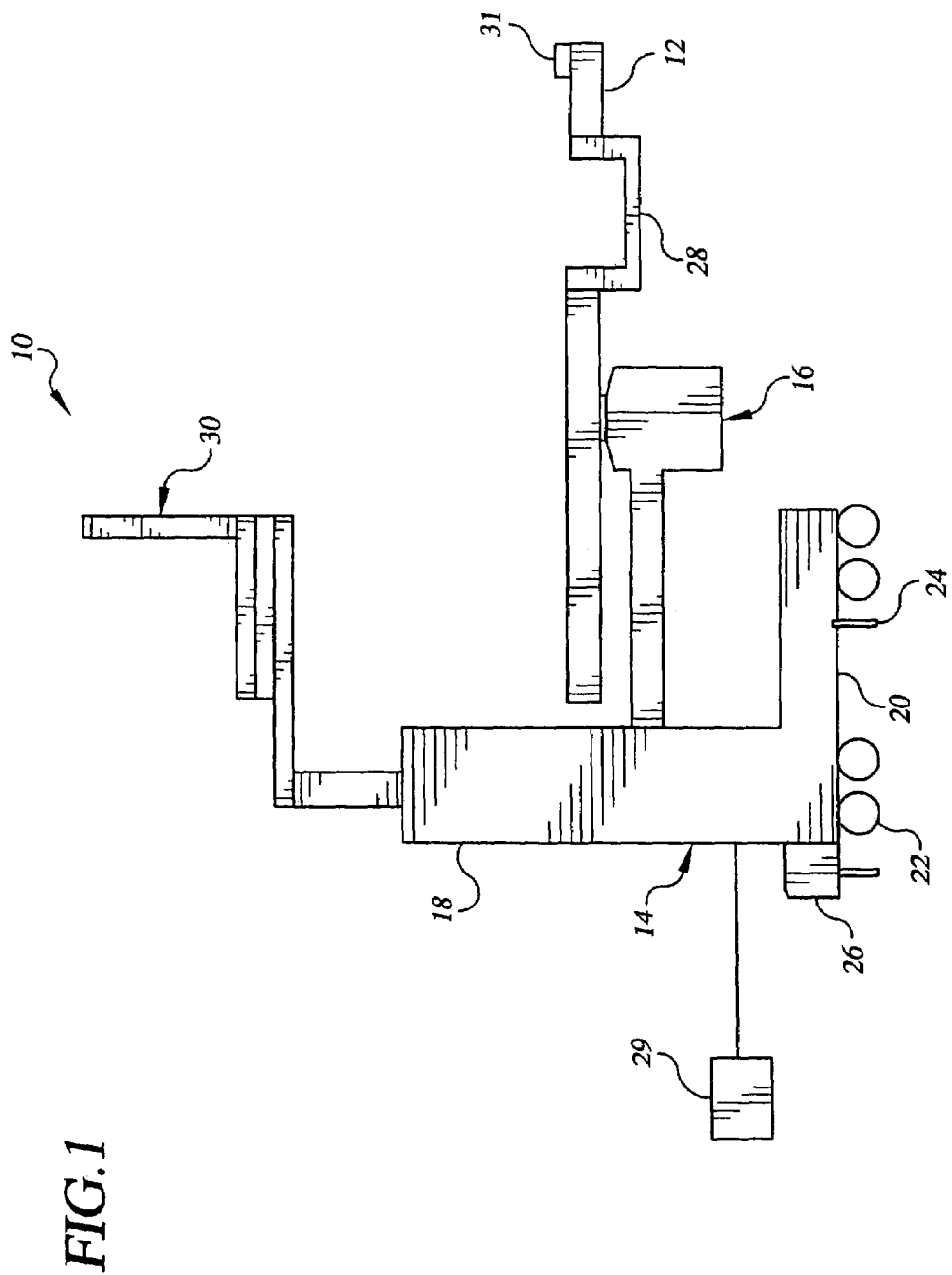
FIG. 1 is a schematic view of one embodiment of the device for aligning a patient for delivering multiple radiation beams according to the present invention.

Referring now to FIG. 1, there is shown a schematic view of one embodiment of the device of the present invention. As can be seen, the device 10 comprises a patient support surface 12, a coarse alignment subsystem 14 connected to the patient support system 12 and a fine alignment subsystem 16 connected to the patient support surface 12.

The coarse alignment subsystem 14 induces coarse movements of the patient support surface 12 around the treatment room. In a preferred embodiment, the coarse alignment subsystem 14 can induce coarse movements of the patient support surface 12 that comprise traversals as large as about 4 m and rotations as large as about 200°. In another preferred embodiment, the coarse alignment subsystem 14 can induce coarse movements of the patient support surface 12 that comprise traversals as large as about 2 m and rotations as large as about 60°. In a particularly preferred embodiment, the coarse alignment subsystem 14 can induce coarse movements of the patient support surface 12 that comprise traversals as large as about 1 m and rotations as large as about 10°.

As shown in FIG. 1, the coarse alignment subsystem 14 comprises an elevating column 18 connected to the fine alignment subsystem 16, and connected to a base 20. The coarse alignment subsystem 14 preferably further comprises a plurality of wheels 22 attached to the base 20, which permit the device 10 to translocate around the treatment room. In one embodiment, the wheels 22 are computer controlled. In another embodiment, the coarse alignment subsystem 14 comprises base stand locks 24 to maintain a selected position of the device 10 in the treatment room. In a preferred embodiment, the coarse alignment subsystem 14 comprises a counterweight 26 connected to the base 20 to counterbalance the weight of the patient support surface 12 and a patient (not shown). Preferably, the coarse alignment subsystem 14 additionally comprises electronics 29 to control movement of the coarse alignment subsystem 14. In one embodiment, the coarse alignment subsystem 14 further comprises a position detection system 30 to calculate the position of the device 10 in the treatment room. A suitable coarse alignment subsystem 14, including a position detection system 30, can be obtained from ONCOlog Medical QA AB of Uppsala, Sweden under the name Hercules, though the belt and belt power stage do not need to be installed for incorporation into the device 10, and the beam axis feature does not need to be used for the device 10. Other commercially available coarse alignment subsystems and position detection systems are also suitable, as will be understood by those with skill in the art with reference to this disclosure.

Figure 2:
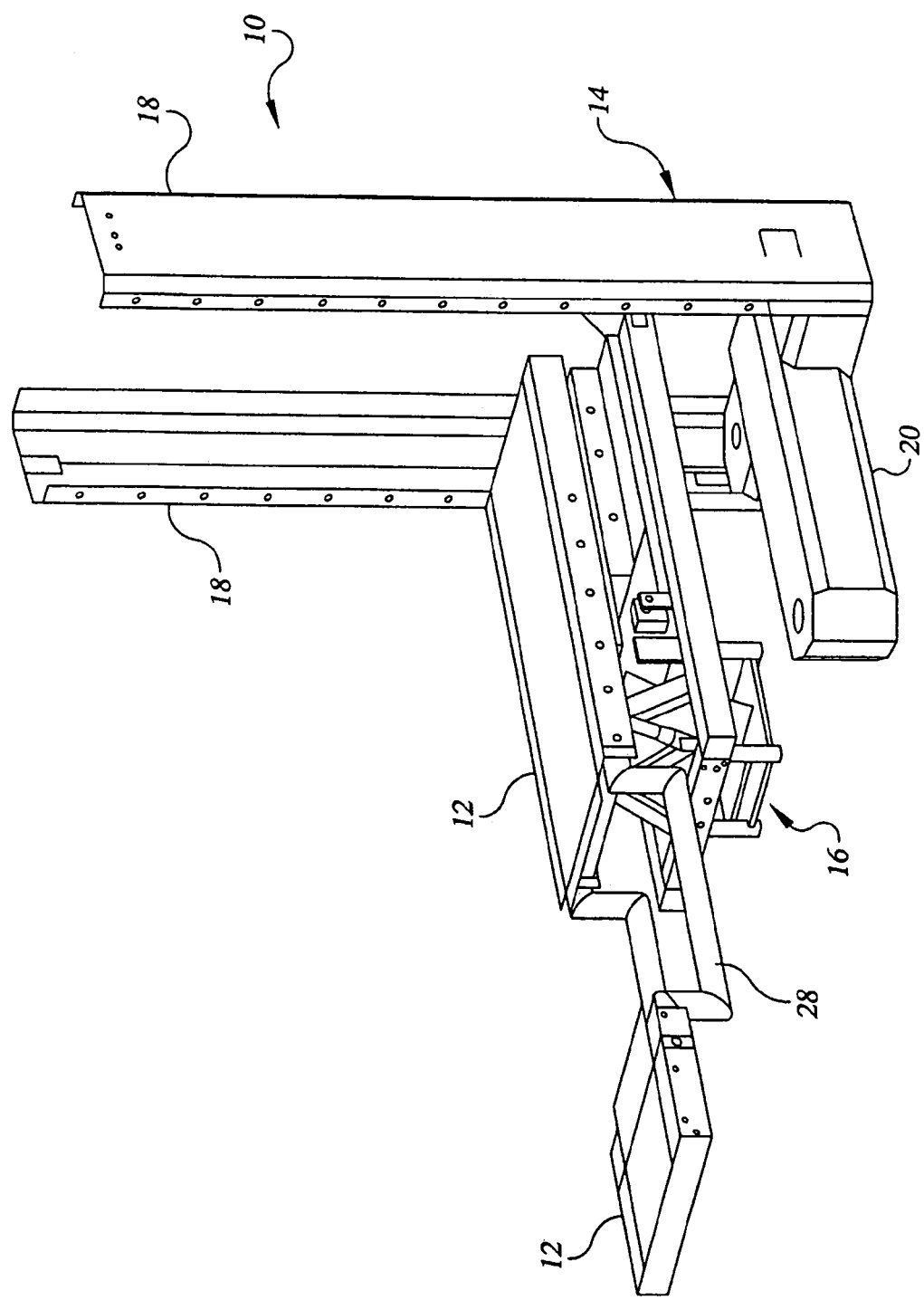
FIG. 2 is a perspective lateral view of the device in FIG. 1 with the patient support surface in a neutral position.

Referring now to FIG. 2, there is shown a perspective side elevational view of the device 10. As can be seen, the device 10 further comprises a patient support surface 12, such as a table. As shown in FIG. 2, the patient support surface 12 is in a neutral position, that is, parallel to the long axis of the base 20 and perpendicular to the long axis of the elevating column 18. A suitable table is the Atlas patient support surface from ONCOlog Medical QA AB, though other patient support surfaces are also suitable, as will be understood by those with skill in the art with reference to this disclosure.

In a preferred embodiment, the device 10 has interfaces 31 for affixing one or more than one registration and immobilization devices, such as whole body pods, foam cradles, face masks, cranial halos and bite blocks. In another preferred embodiment, as shown, the patient support surface 12 comprises an opposing pair of C-shaped arms 28 that link one part of the patient support surface 12 to another part along its longitudinal length and that allow the distal end of the patient support surface 12 to extend distally, creating an open area that allows a radiation beam to pass into the target tissue unimpeded while the patient remains supported by one or more than one registration device. Preferably, the C-shaped arms 28 can be rotated away from the beam path while the patient is registered and immobilized on the patient support surface 12.

The device 10 further comprises a fine alignment subsystem 16 connected to the patient support surface 12 and to the coarse alignment subsystem 14. The fine alignment subsystem, 16 induces fine movements of the patient support surface 12 with respect to the treatment room. In one embodiment, the fine movements comprise translation motions of as large as about ±20 mm with between about 0.04 mm and 0.1 mm resolution in three perpendicular axes, and pitch and roll rotations of as large as about ±5° with a resolution of between about 0.1° and 0.2°. In a preferred embodiment, the fine movements comprise translation motions of as large as about ±20 mm with about 0.05 mm resolution in three perpendicular axes, and pitch and roll rotations of as large as about ±5° with a resolution of about 0.1°.

Figure 3:
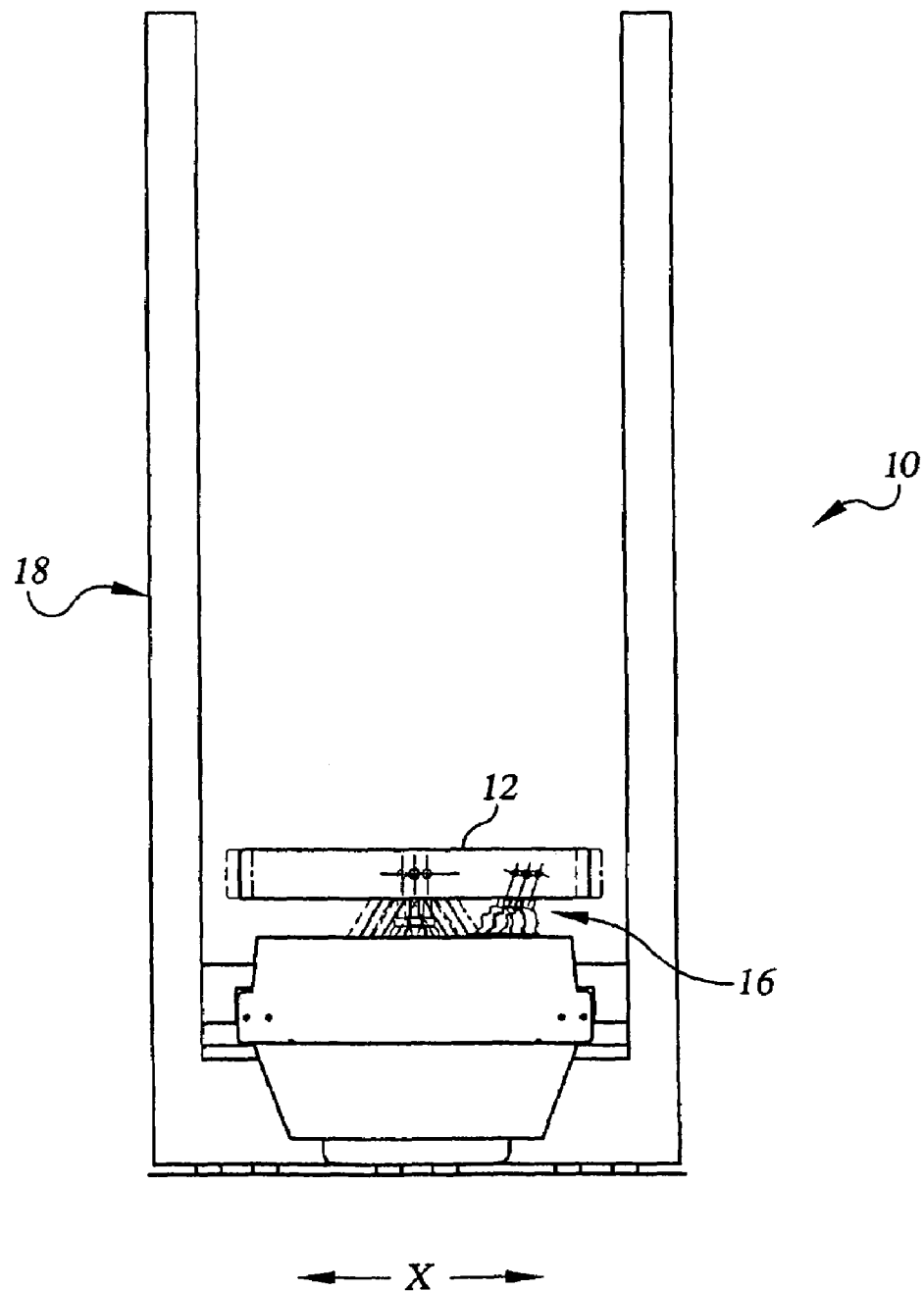
FIG. 3 is a side elevational schematic view of the device in FIG. 1 showing fine movement of the device in the x-axis.
Figure 4:
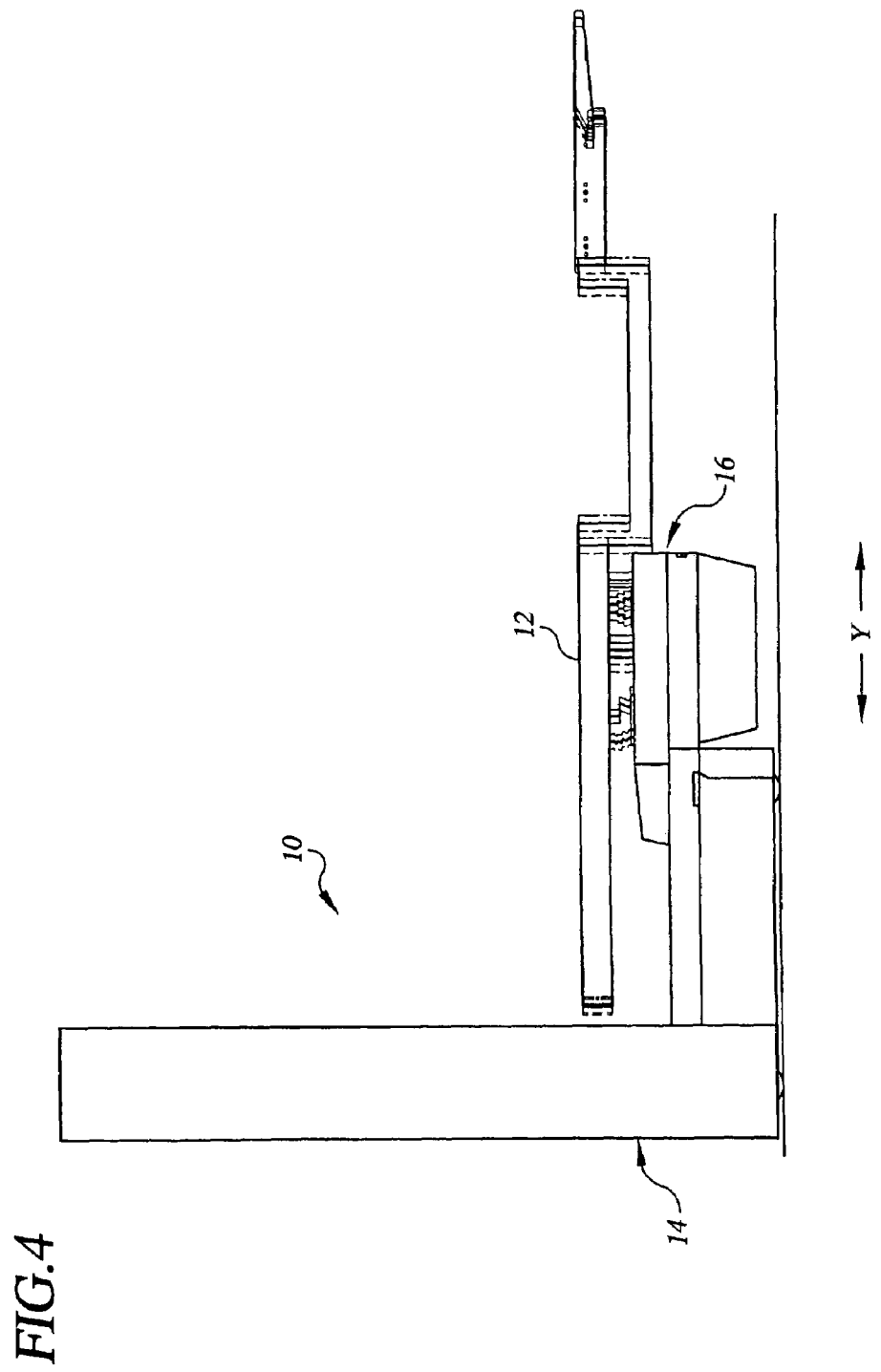
FIG. 4 is a side elevational schematic view of the device in FIG. 1 showing fine movement of the device in the y-axis.
Figure 5:
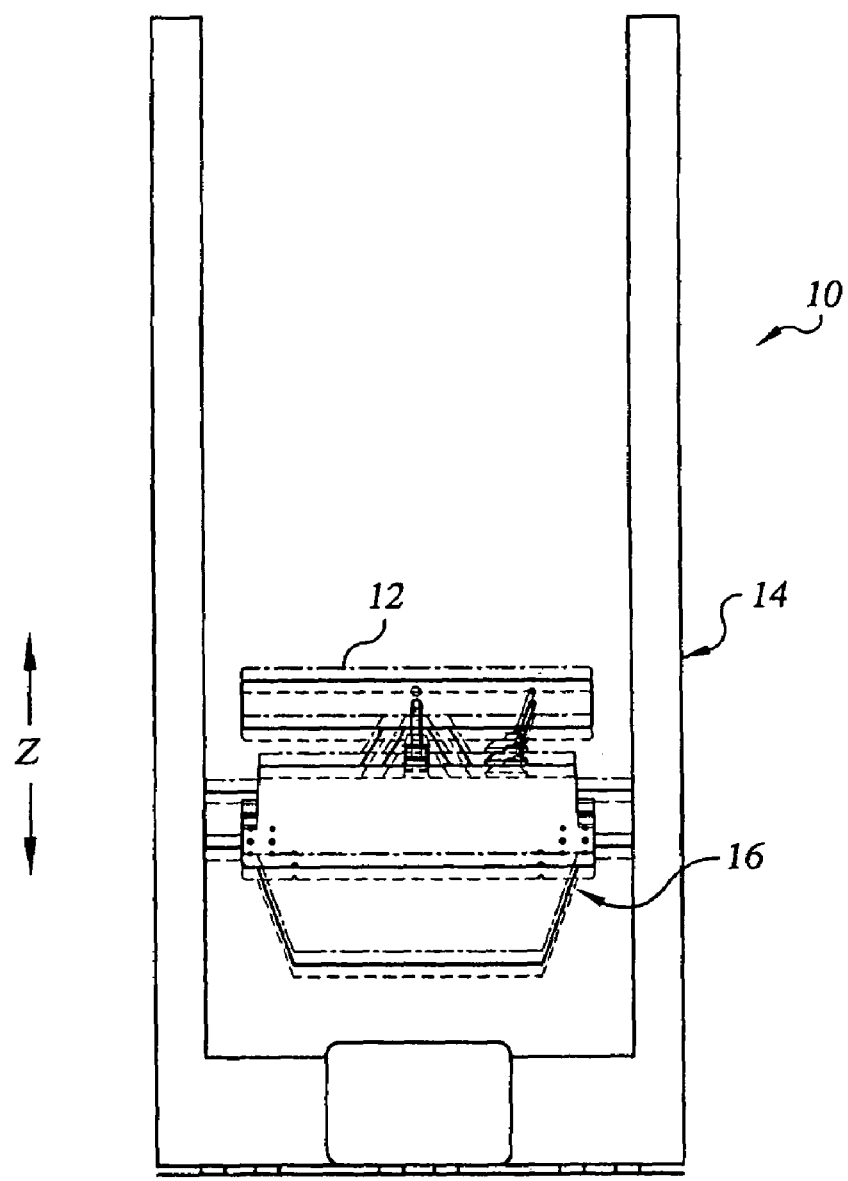
FIG. 5 is a side elevational schematic view of the device in FIG. 1 showing fine movement of the device in the z-axis.
Figure 6:
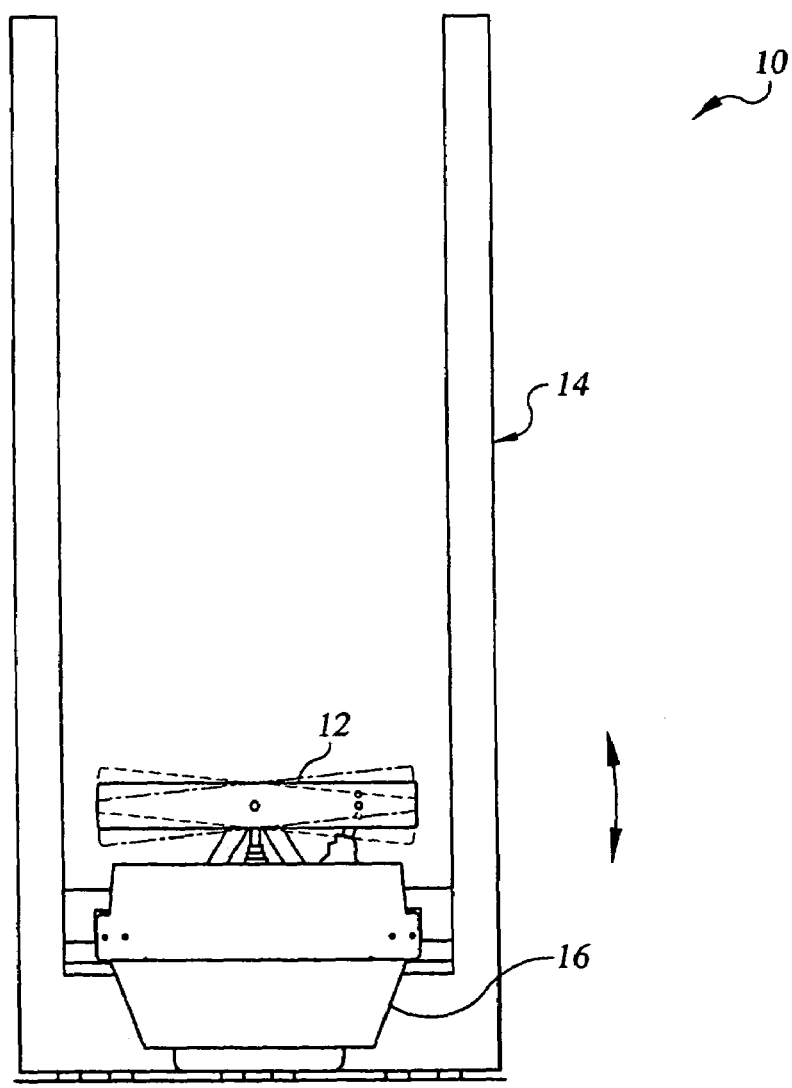
FIG. 6 is a side elevational schematic view of the device in FIG. 1 showing fine movement of the device in a roll motion.
Figure 7:
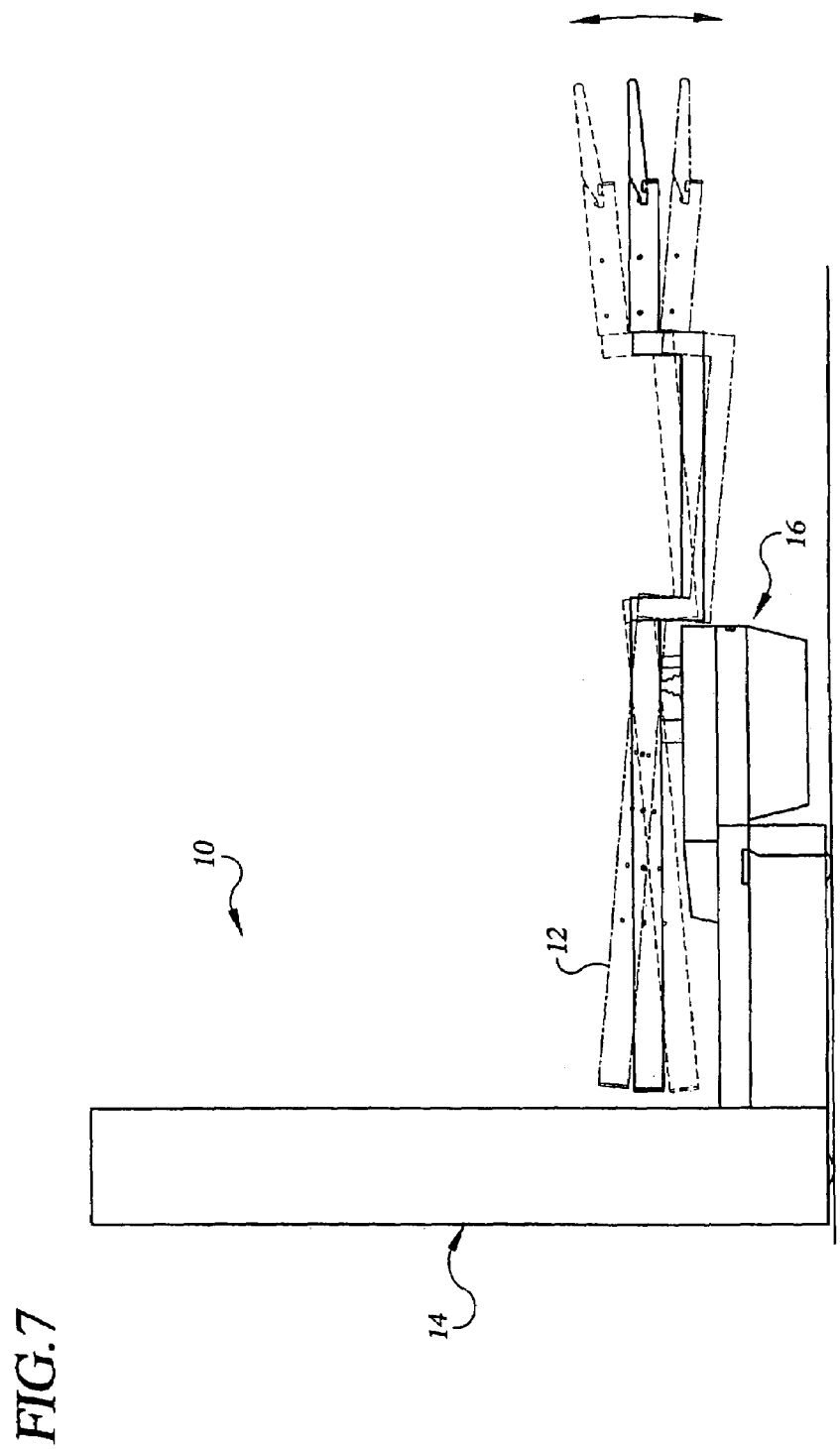
FIG. 7 is a side elevational schematic view of the device in FIG. 1 showing fine movement of the device in a pitch motion.

Referring now to FIG. 3 through FIG. 7, there are shown side elevational schematic views of the device 10 showing: fine movement of the device 10 in the x-axis, FIG. 3; fine movement of the device 10 in the y-axis, FIG. 4; fine movement of the device 10 in the z-axis, FIG. 5; fine movement of the device 10 in a roll motion, FIG. 6; and fine movement of the device 10 in a pitch motion, FIG. 6.

Figure 8:
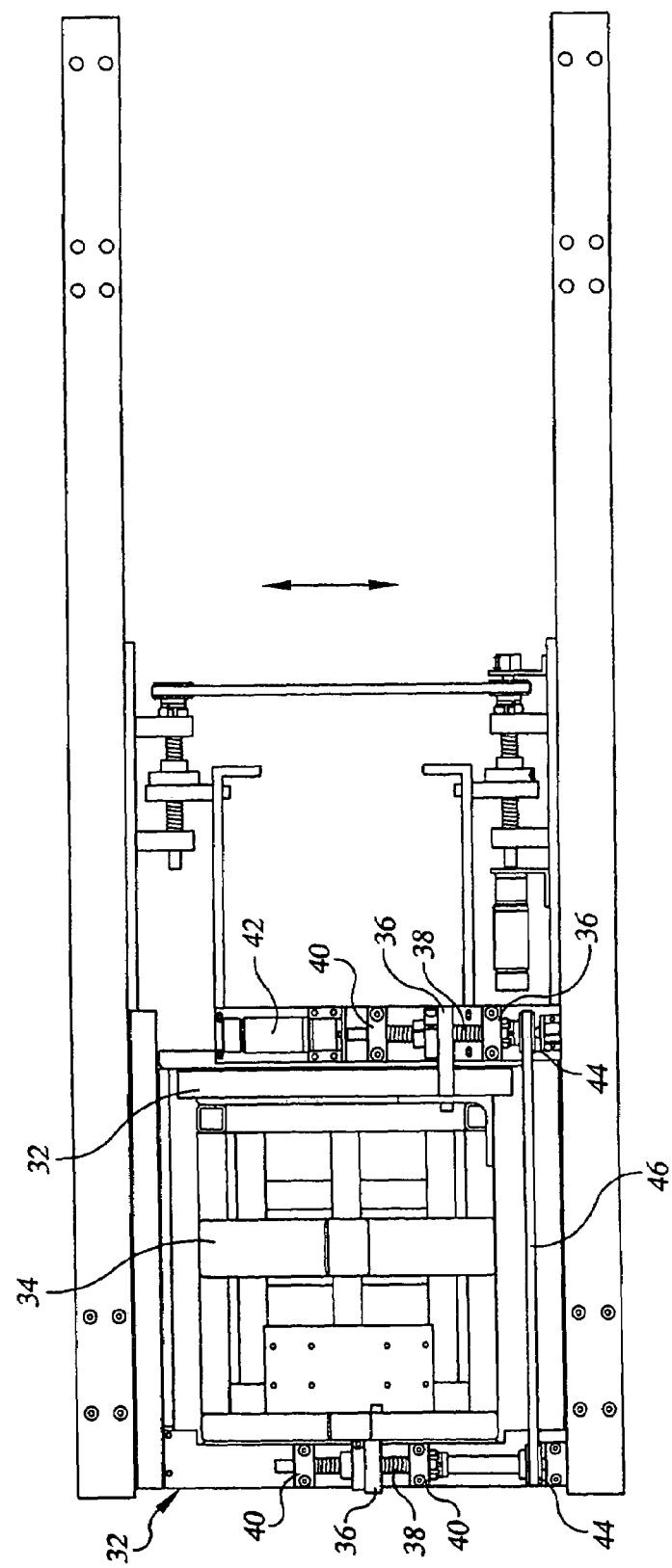
FIG. 8 is a top cutaway, schematic view of the device in FIG. 1 illustrating an example of the components of the device in FIG. 1 allowing for fine movement in the x-axis.

Referring now to FIG. 8, there is shown a top cutaway, schematic view of the device 10 illustrating an example of the components of the device 10 allowing for fine movement in the x-axis. As can be seen, the components of the device 10 allowing for fine movement in the x-axis comprise rails 32, an x-carrier 34, a driver slot with a ball nut 36, a ball screw 38, a bearing holder 40, a motor with gearbox 42, belt pulleys 44, a synchronizing belt 46, and a 10-turn precision potentiometer 48.

Figure 9:
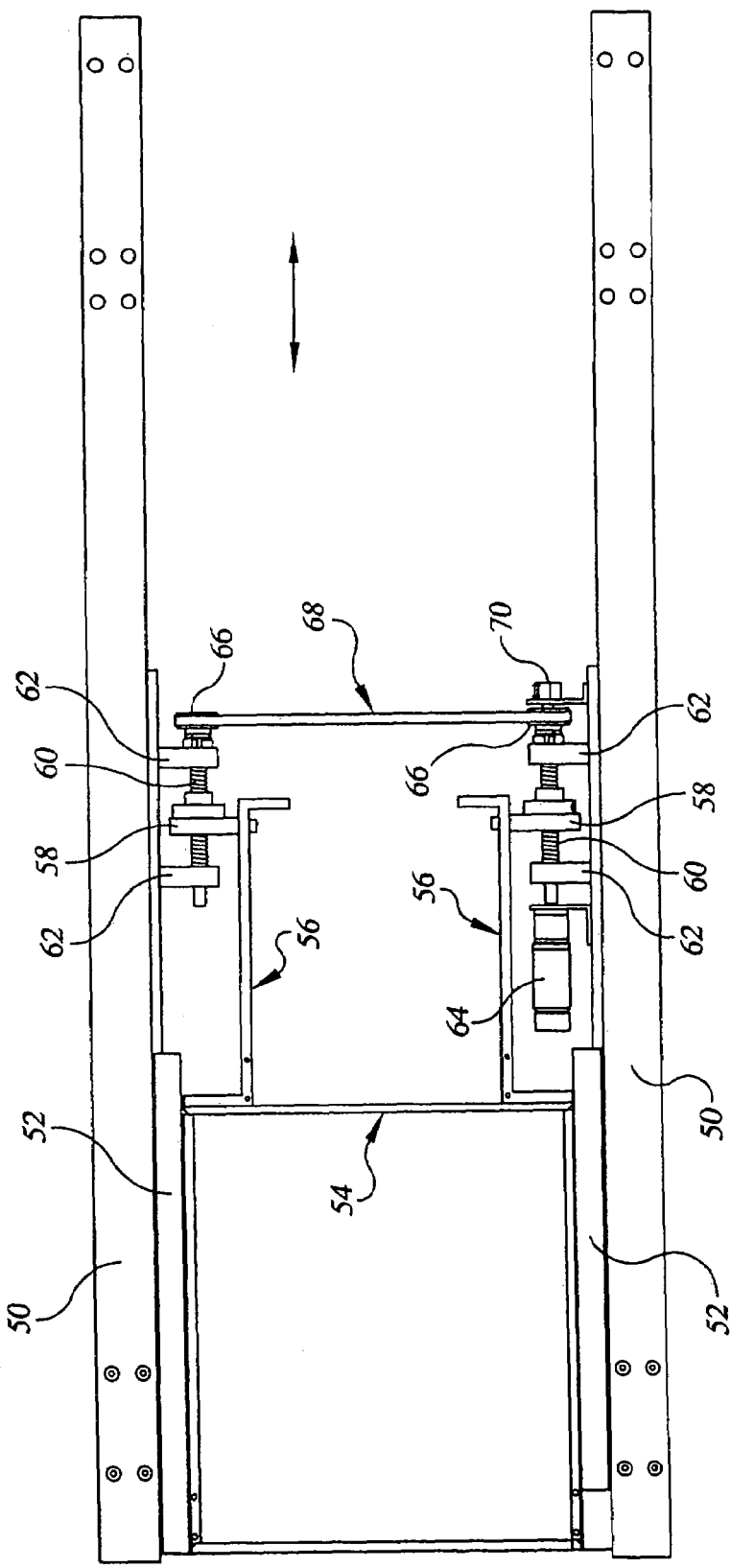
FIG. 9 is a top cutaway, schematic view of the device in FIG. 1 illustrating an example of the components of the device in FIG. 1 allowing for fine movement in the y-axis.

Referring now to FIG. 9, there is shown a top cutaway, schematic view of the device 10 illustrating an example of the components of the device 10 allowing for fine movement in the y-axis. As can be seen, the components of the device 10 allowing for fine movement in the y-axis comprise a framework 50, rails 52, a y-carrier 54, a support driver 56, a driver slot with a ball nut 58, a ball screw 60, a bearing holder 62, a motor with gearbox 64, belt pulleys 66, a synchronizing belt 68, and a 10-turn precision potentiometer 70.

Figure 10:
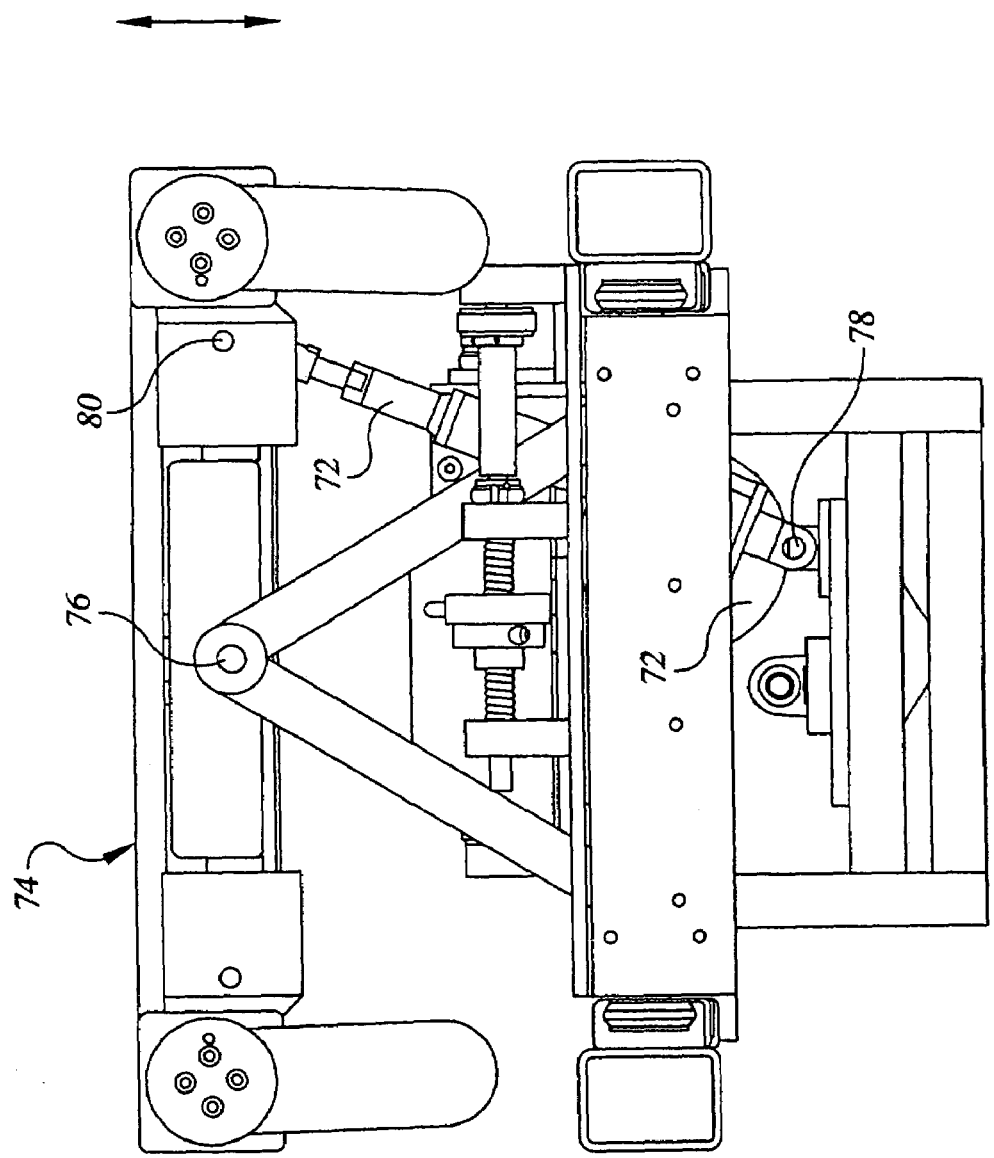
FIG. 10 is a top cutaway, schematic view of the device in FIG. 1 illustrating an example of the components of the device in FIG. 1 allowing for fine roll movement.

Referring now to FIG. 10 there is shown a lateral cutaway, schematic view of the device 10 illustrating an example of the components of the device 10 allowing for fine roll movement. As can be seen, the components of the device 10 allowing for fine roll movement comprise a linear actuator 72, a tabletop 74, a center of rotation for roll angle 76, a lower center of rotation for the actuator 78, and an upper center of rotation for the actuator 80. Also shown are the C-shaped arms 28.

Figure 11:
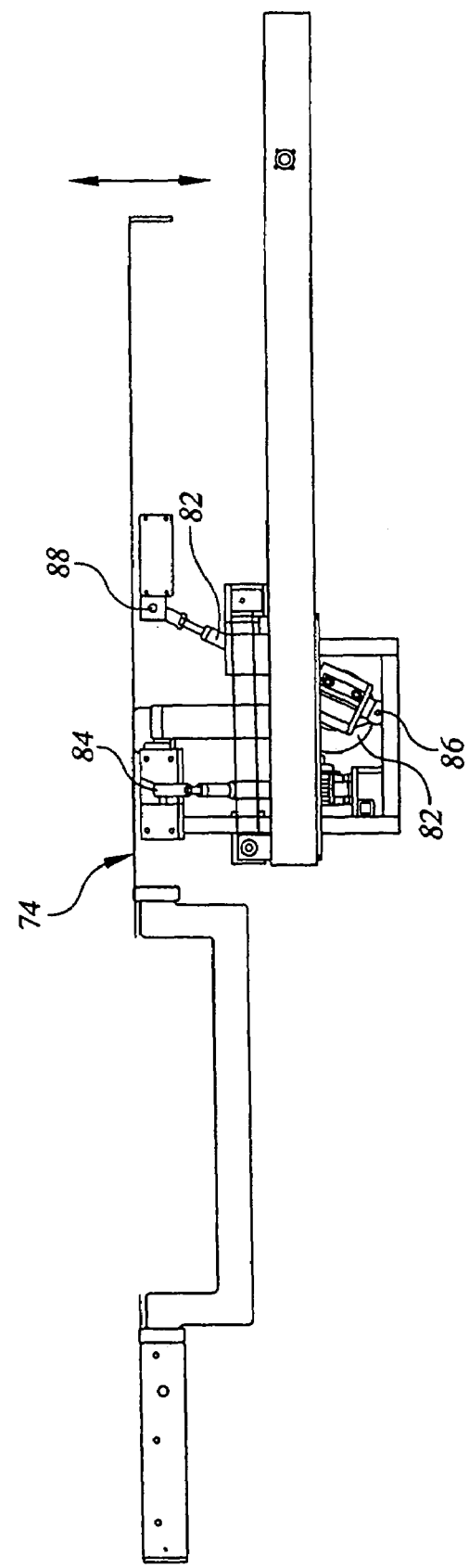
FIG. 11 is a perspective cutaway, schematic view of the device in FIG. 1 illustrating an example of the components of the -device in FIG. 1 allowing for fine pitch movement.
Figure 15:
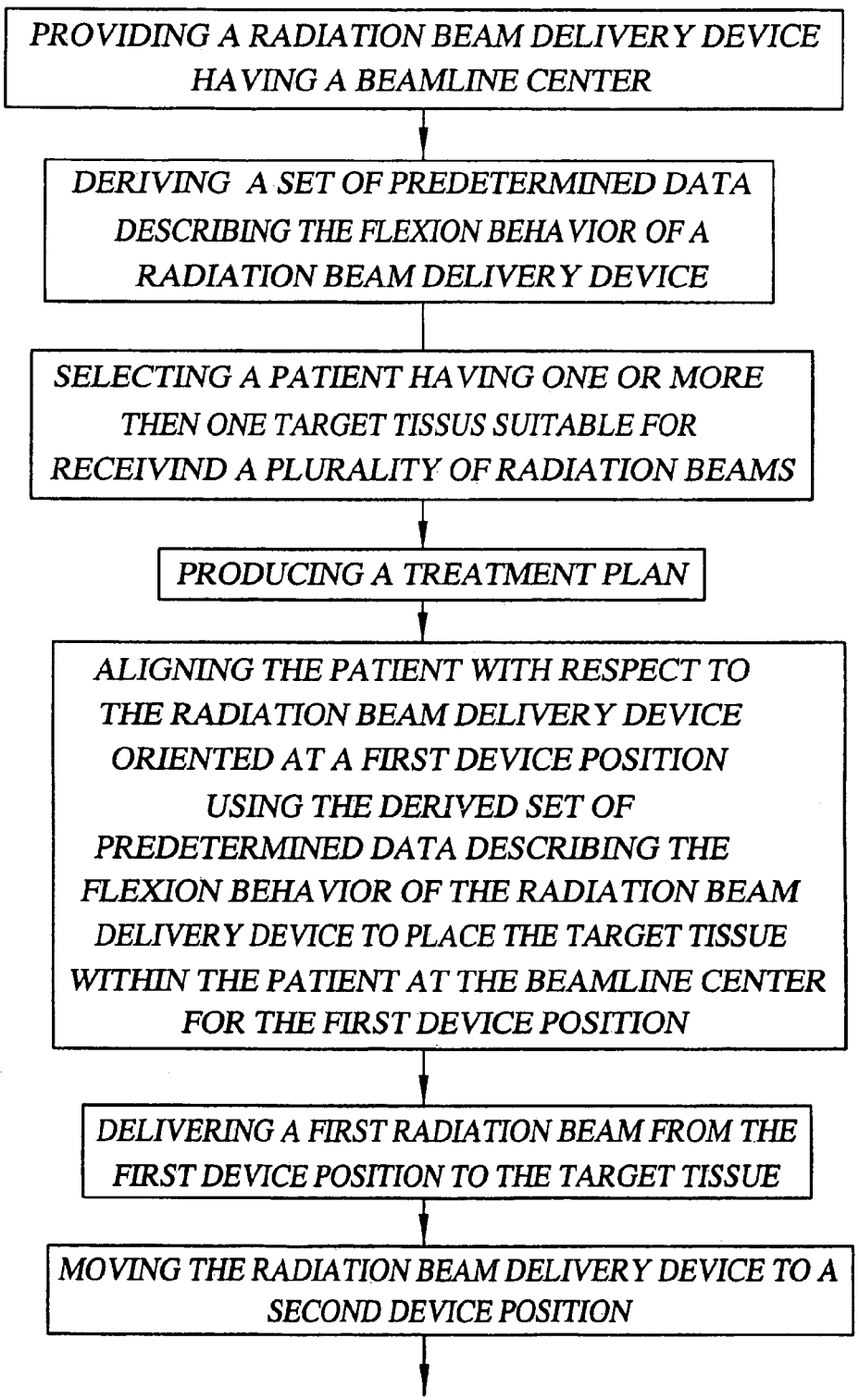

Referring now to FIG. 11 there is shown a lateral cutaway, schematic view of the device 10 illustrating an example of the components of the device 10 allowing for fine pitch movement. As can be seen, the components of the device 10 allowing for fine pitch movement 5 comprise a linear actuator 82, a tabletop 74, a center of rotation for pitch angle 84, a lower center of rotation for the actuator 86, and an upper center of rotation for the actuator 88.

In another embodiment of the present invention, there is provided a method of aligning a patient for delivering a plurality of radiation beams, such as proton beams, from a radiation beam delivery device at a plurality of device positions. Referring now to FIG. 12, FIG. 13, FIG. 14 and FIG. 15, there are shown flow charts depicting some steps of various embodiments of the method of the present invention. The method comprises compensating for flexion of a radiation beam delivery device within a gantry during movement of the radiation beam delivery device from a first device position to a second device position by using a set of predetermined data describing the flexion behavior of the radiation beam delivery device so that the target tissue within the patient is placed at the beamline center for the radiation beam delivery device at the second device position. The method allows a patient to be irradiated from a plurality of delivery device positions without the patient undergoing a full realignment procedure between repositioning of the radiation beam delivery device from the first device. position to the second device position. The method advantageously reduces the time and cost for delivering a plurality of radiation beams from a plurality of device positions.

The present method of aligning a patient for delivering a plurality of radiation beams from a plurality of device positions comprises the following steps. First, a set of data describing the flexion behavior of a radiation beam delivery device during repositioning is derived. Next, a suitable patient is selected, where the patient has one or more than one target tissue suitable for receiving a plurality of radiation beams. Then, a treatment plan is produced. Next, the patient is aligned with respect to a reference set-up position to place the target tissue within the patient at the isocenter. Then, the radiation beam delivery device is moved to a first device position. Next, flexion of the radiation beam delivery device produced by the move to the first device position is compensated for using the set of predetermined data describing the flexion behavior of the radiation beam delivery device to place the target tissue within the patient at the beamline center for the radiation beam delivery device at the first device position. Then, a first radiation beam from the radiation beam delivery device at the first device position is delivered to the target tissue within the patient. Next, the radiation beam delivery device is moved to a second device position. Then, flexion of the radiation beam delivery device produced by the move to the second device position is compensated for using the set of predetermined data describing the flexion behavior of the radiation beam delivery device to place the target tissue within the patient at the beamline center for the radiation beam delivery device at the second device position. Next, a second radiation beam from the radiation beam delivery device at the second device position is delivered to the target tissue within the patient.

In one embodiment, the radiation beam delivery device is moved to a third device position. Then, flexion of the radiation beam delivery device produced by the move to the third device position is compensated for using the set of predetermined data describing the flexion behavior of a radiation beam delivery device derived previously. Next, a third radiation beam from the radiation beam delivery device at the third device position is delivered to the target tissue within the patient. As will be understood by those with skill in the art with reference to this disclosure, additional radiation beams from additional device positions can be delivered to the target tissue within the patient by compensating for flexion of the radiation beam delivery device produced by the move to the additional device positions using the set of predetermined data describing the flexion behavior of a radiation beam delivery device. Each of these steps will now be disclosed in greater detail. First, a set of data describing the flexion behavior of a radiation beam delivery device is derived. Referring now to FIG. 16 and FIG. 17, there are shown plots of combined data sets describing the flexion behavior of two sample radiation beam delivery devices at the Loma Linda University Proton Treatment Facility, Loma Linda, Calif., US, in the plane of gantry rotation, FIG. 16, and perpendicular to the plane of gantry rotation, FIG. 17. The measurements were made as follows.

Measurement of the mechanical isocenter was divided into two perpendicular components. The first component was used to describe the radial deviation as the gantry rotates, while the second component describes the axial runout. The radial component was measured by first inserting a milled block into the end of the beam delivery device closest to where the patient would be located during a treatment. The milled block extended from the delivery device to beyond the estimated virtual center of the gantry. A theodolite with a 32× magnification telescope was placed in the room approximately three meters from the presumed isocenter and coaxially with it. A grid on the block was observed through the theodolite telescope while the gantry was rotated in increments of 10°. After each movement, the coordinate of the cross in the theodolite sight relative to the grid was recorded. After the data were measured, they were transformed from the gantry coordinate system to the room coordinate system and plotted. The axial runout was measured with a dial indicator that was rigidly affixed to the end of the patient positioner with its sensitive point touching the milled block at the previously determined radial isocenter. Again, the gantry was rotated in increments of 10°, stopping to record the measurements. Both radial and axial tests were performed in the clockwise and counterclockwise directions. Circles represent the path of the beamline center during a clockwise rotation while crosses represent the path of the beamline center during a counter clockwise rotation.

Next, a suitable patient is selected, where the patient has one or more than one target tissue suitable for receiving a plurality of radiation beams. A suitable patient will be one having one or more than one target tissue having a disease or condition amenable to teletherapy, such as a solid tissue neoplasm, an arterio-venous malformations or Parkinson's disease. In a preferred embodiment, the patient will have a solid tissue neoplasm susceptible to radiation therapy, such as a neoplasm selected from the group consisting of acoustic neuroma, adenocarcinoma, astrocytoma, chordoma, meningioma, nasopharyngeal carcinoma and pituitary adenoma.

Then, a treatment plan is produced using conventional methods. For example, the patient is registered and immobilized to a patient positioner of a scanner, such as an XCT scanner or other suitable device, using appropriate registration and immobilization procedures, and the patient is scanned. The information from the scan is then transferred to a treatment planning system, and the treatment plan is produced.

Next, the patient is aligned such that the target tissue within the patient is at the beamline center of the radiation beam delivery device for delivering a first beam of radiation to the target tissue. In one embodiment, the patient is aligned using a two-stage patient positioner device for aligning a patient for delivering a plurality of radiation beams according to the present invention. This can be accomplished, for example as follows.

FIG. 18 is a flowchart illustrating one embodiment of a method of positioning a patient for receiving radiation treatment. First, the target location within the patient is determined relative to a reference point of the patient positioner. Then, the room coordinates for the patient positioner coarse alignment subsystem that are required to place the radiation beam delivery device beamline center at the target location within the patient are calculated, and these coordinates are transferred into a patient positioner database to generate a position file. Next, the patient is taken to the treatment room and the patient is registered and immobilized to the patient positioner using the identical registration and immobilization devices used for generating the treatment plan. Then, the fine alignment subsystem is centered to a neutral position and the coarse alignment subsystem is used to place the target tissue within the patient close to the beamline center for the radiation beam delivery device using the reference point of the patient positioner. Then, the target tissue location is determined using conventional methods, such as using localization x-ray images, and any discrepancy between the target tissue's present location and the target tissue's desired location is calculated. Next, the patient positioner fine alignment subsystem is used to place the target tissue within the patient at the beamline center for the radiation beam delivery device at the first device position.

After the patient is aligned, a first radiation beam from the first device position is delivered to the target tissue within the patient. Next, the radiation beam delivery device is moved to a second device position. Then, flexion of the radiation beam delivery device produced by the move to the second device position is compensated for using the set of predetermined data describing the flexion behavior of the radiation beam delivery device so that the target tissue within the patient is placed at the beamline center for the radiation beam delivery device at the second device position. In a preferred embodiment, compensation is accomplished by moving the patient and patient positioner as a unit, such as by using a two-stage patient positioner device according to the present invention. In another preferred embodiment, compensation is accomplished by one or more than one action selected from the group consisting of shifting an aperture or block holding cone with respect to the center of the beam delivery apparatus, shifting the position of the defining collimators of the beam delivery apparatus (such as the leaves of a multi-leaf collimator), and offsetting the scan pattern of a magnetically scanned beam, where each of these actions can be combined with rotation of the gantry as necessary to maintain the direction and the aiming point of the beam, as will be understood by those with skill in the art with reference to this disclosure. Next, a second radiation beam from the second device position is delivered to the target tissue within the patient.

The present method can also be used with other therapy delivery techniques, including serial (fan beam) tomotherapy, spiral (helical) tomotherapy, intensity modulated arc therapy (IMAT), cone beam dynamic therapy (sliding window), or cone beam segmental therapy (step and shoot), as well as being used for diagnostic radiation exposures, as will be understood by those with skill in the art with reference to this disclosure.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A method of aligning a patient for delivery of radiation therapy to a treatment area of the patient, the patient being positioned on a patient positioner configured to move the patient with respect to a radiation delivery device, the method comprising:
   (a) at a first location,
      determining a relationship between the treatment area and a reference point of the patient positioner;
      calculating location coordinates for the patient positioner based on the relationship between the treatment area and the reference point;
   (b) at a second location,
      immobilizing the patient on the patient positioner;
      adjusting a position of the patient positioner according to the calculated location coordinates so that the treatment area is approximately aligned with a beamline center of the radiation delivery device, wherein the time required for alignment of the patient at the second location is minimized due to the calculation of location coordinates at the first location; and
   (c) activating the radiation delivery device in order to deliver radiation to the treatment area of the patient.

2. A method of aligning a patient for delivery of radiation therapy to a treatment area of the patient, the patient being positioned on a patient positioner configured to move the patient with respect to a radiation delivery device, the method comprising:
   (a) at a first location,
      determining a relationship between the treatment area and a reference point of the patient positioner;
      calculating location coordinates for the patient positioner based on the relationship between the treatment area and the reference point; and
   (b) at a second location,
      immobilizing the patient on the patient positioner;
      adjusting a position of the patient positioner according to the calculated location coordinates so that the treatment area is approximately aligned with a beamline center of the radiation delivery device, wherein the time required for alignment of the patient at the second location is minimized due to the calculation of location coordinates at the first location.
   (c) determining a precise target area within the treatment area using localized x-ray images;
   (d) calculating a difference between the beamline center of the radiation delivery device and the precise target area based on the localized x-ray images; and (e) adjusting a position of the patient positioner according to the calculated difference so that the precise target area is aligned with the beamline center of the radiation delivery device.

3. The method of claim 1, wherein the first location is a treatment planning room.

4. The method of claim 1, wherein the second location is a treatment room.

5. The method of claim 1, wherein the radiation delivery device delivers proton radiation.

6. A system for positioning a patient for delivery of a plurality of radiation beams in a treatment room, the system comprising:
- a patient support surface for supporting the patient within the treatment room;
- a patient positioner database storing position data indicating a relationship between a previous position of the patient outside of the treatment room and a stationary location outside of the treatment room;
- a first subsystem configured to access the position data and to induce course movements of the patient support surface based at least partly upon the received position data; and
- a second subsystem configured to induce fine movements of the patient support surface.

7. The system of claim 6, wherein the position data comprises coordinates for aligning the patient positioner so that a radiation beam delivery device beamline is center at a target location within the patient.

8. The system of claim 6, wherein the position data is determined in a treatment planning room with the patient positioned on the patient support surface and, after determination of the treatment data, the patient support surface is moved to a treatment room housing the first and second subsystems.

9. The system of claim 6, wherein the fine movements comprise submillimeter translations.

10. The system of claim 6, wherein the fine movements comprise subdegree rotations.

11. The system of claim 6, wherein the fine movements comprise translations in three perpendicular axes.

12. The system of claim 6, wherein the course movements comprise translation motions of as large as approximately two meters.

13. The system of claim 6, wherein the course movements comprise rotations of as large as approximately sixty degrees.

14. The system of claim 6, wherein the second subsystem further comprises a linear actuator coupled to the patient support surface.

15. The system of claim 6, wherein the linear actuator is configured to induce roll movement of the patient support surface.

* * * * *